United States Patent [19]
Chang

[11] Patent Number: 5,984,952
[45] Date of Patent: Nov. 16, 1999

[54] FACIAL STEAMER WITH AN ADJUSTABLE STEAMER ARM

[76] Inventor: Henry Ping Chang, 2345 Ridge Way, San Marino, Calif. 91108

[21] Appl. No.: 08/901,160

[22] Filed: Jul. 28, 1997

[51] Int. Cl.$^6$ ...................................................... A61F 7/00
[52] U.S. Cl. ............................................ 607/109; 607/96
[58] Field of Search ..................... 607/96, 104, 107–112, 607/83; 126/204

[56] References Cited

U.S. PATENT DOCUMENTS

| | | |
|---|---|---|
| 3,768,483 | 10/1973 | Kusunoki . |
| 4,190,052 | 2/1980 | McCarthy . |
| 4,274,588 | 6/1981 | Schwob ................................... 239/138 |
| 4,292,971 | 10/1981 | Smit et al. . |
| 4,616,122 | 10/1986 | Burian et al. ............................ 219/273 |
| 5,010,905 | 4/1991 | Snyder et al. ........................... 132/272 |

OTHER PUBLICATIONS

Catalog sheet for "Eight–function Combination Skin Care System", by Bio Jouvance, 1998.

Primary Examiner—Linda C. M. Dvorak
Assistant Examiner—Roy Gibson
Attorney, Agent, or Firm—David and Raymond; Raymond Y. Chan

[57] ABSTRACT

A facial steamer having an adjustable steamer arm, which includes a steamer spread arm, a first adjustable device, a second adjustable device hingedly and rotatably connect to the first adjustable device by means of two connecting means, a steam transporting mean, and a mounting device for rotatably mounting the second adjustable device in position, enables the adjustable steamer arm to be selectively rotated along an connecting axis thereof and swung up and down for enabling the cosmetician to selectively adjust the adjustable steamer arm to an adequate position with respect to the face position of the patient more easily. Moreover, the facial steamer is specifically designed to be located at a hand reaching position close to the cosmetician for ensuring easy operation.

18 Claims, 7 Drawing Sheets

FACIAL STEAMER WITH AN ADJUSTABLE STEAMER ARM

FIELD OF THE PRESENT INVENTION

The present invention relates to a facial steamer, and more particularly to a facial steamer having an adjustable steamer arm adapted to be selectively rotated and swung within a predetermined angular displacement for enabling the cosmetician to adjustably position the adjustable steamer arm with respect to the face position of the patient more easier while the facial steamer is capable of positioning closely to the cosmetician to ensure easy operation.

BACKGROUND OF THE PRESENT INVENTION

There is an old saying that: "loving to look beautiful is a first nature of woman". That is definitely a true statement but, nowadays, even men are paying more attention to their outlook than before. In today's society, people are unavoidably to judge you by how you look because it is the first resource that you present yourselves to others. Therefore, in order to look younger and healthier, it is getting more and more popular for people spending time to have facial care in beauty shop to protect their skin and to clean their faces by utilizing the facial steamer. Many men and women go to the beauty shop to have their faces done on a weekly basis. The facial steamer can supply atomized steam spreading onto a patient's face skin for cleaning and relaxing purposes. After the skin is spread with the atomized steam, the cosmetician can massage the skin and clean out the dirt particle from the pores of the skin.

As shown in FIG. 1A, a first generation facial steamer on the market is simply a very basic equipment, that comprises only a steamer device 100 and a steamer arm 101 rigidly extending from the steamer device. A far end of the steamer arm provided a steam outlet opening 102 for spreading out steam at a fixed angle that can not be adjusted to other desirable position.

A second generation facial steamer, as shown in FIG. 1B, has been improved over the first generation facial steamer, in which a steamer arm 201 is reconstructed to rotatably attach on a side of a steamer device 200 so that the steamer are 201 is able to be adjusted with certain rotating angle. Even though the second generation facial steamer provides plenty of improvement over the first generation facial steamer, the rotatably angle is only limited to unidirectional movement.

In view of such limited rotatable angle of the conventional facial steamer, it causes the following shortcomings:

a) As shown in FIG. 1C, the patient P usually is required to lay on an operation bed while the cosmetician C sits or stands at an end side of the operation bed in order to work on the patient's face. Due to the limited unidirectional rotation movement of the facial steamer arm 201, the control panel 203 having all operation buttons of the facial steamer provided thereon is unavoidably positioned far away from the sitting position of the cosmetician C, so that the cosmetician is unable to directly hand reaching the control panel 203 without the need of standing up or even walking around the facial steamer 200 to operate those operation buttons provided on the control panel 203. That causes great inconvenience for the cosmetician.

b) Since the facial steamer arm 201 is only adjustable within the limited unidirectional rotation movement, the steam outlet opening 202 disposed on the facial steamer arm 201 can only be fixed at a certain discharging angle to spread the steam on the face skin of the patient.

c) When the cosmetician needs to adjust the facial steamer arm to spread steam on some other adjacent portion of the patient, the cosmetician must move the whole facial steamer instead of just the facial steamer arm.

SUMMARY OF THE PRESENT INVENTION

The main objective of the present invention is to provide a facial steamer with an adjustment facial steamer arm connected to a steam generating means, wherein the adjustable steamer arm is adapted to be selectively rotated along an connecting axis thereof and swung up and down for enabling the cosmetician to selectively adjust the adjustable steamer arm to an adequate position with respect to the face position of the patient more easier. Moreover, the facial steamer is specifically designed to be located at a hand reaching position closely to the cosmetician for ensuring easy operation.

Another objective of the present invention is to provide a facial steamer with an adjustable steamer arm, wherein its steam outlet can be rotated by rotating the adjustable steamer arm within a wide angle between an upper position and a lower position in order to adapt for various steam applying angles and purposes to fulfill different patients' need.

Another objective of the present invention is to provide a facial steamer with an adjustable steamer arm which comprises a steam transmitting means for ensuring a fluent passage for the steam generated from the steam generating means even when the adjustable steamer arm is swung to bend.

Another objective of the present invention is to provide a facial steamer with an adjustable steamer arm, in which the rotating angle of the adjustable steamer arm is operationally limited by a rotation displacement limiter to prevent the electrical wires extending from the steam generating means to the adjustable steamer arm being tangled up.

Accordingly, a facial steamer, comprising a steam generating means for generating steam and an adjustable steamer arm connected to the steam generating means, the steam generating means comprising a movable steamer housing having a front operation control panel for controlling a plurality of operational functions of the steam generating means and a side connecting plate for mounting the adjustable steamer arm thereto.

The adjustable steamer arm comprising a steamer spread arm having a steam outlet thereon, a first adjustable device connected with the steamer spread arm, a second adjustable device hingedly and rotatably connected to the first adjustable device by a first and a second connecting means, a steam transporting means for transmitting steam generated from the steam generating means to exit through the steam outlet of the steamer spread arm via the first adjustable device and the second adjustable device, and a mounting device installed inside the steamer housing for rotatably mounting the second adjustable device to the side connecting plate of the steam generating means.

The first adjustable device comprising a hollow cover tube with a predetermined diameter and a first turning connector, the hollow cover tube having a first end connected to the first turning connector and a second end is connected to the steamer spread arm.

The second adjustable device comprising a second turning connector which is rotatably and hingedly connected with the first turning connector, a rotation displacement limiter for rotatably connecting the second turning connector to the mounting device and limiting a rotation angle of the second turning connector with respect to the mounting device, and a friction resistance ring enwrapped the rotation displacement limiter for reducing friction therebetween; so that the first adjustable device is able to swing up and down with respect to the second adjustable device, and that the second adjustable device is able to rotate with respect to the steam generating means.

The steam transporting mean comprising a first pipe, a second pipe, a heat resistant flexible connecting tube, and a supporting spring, in which the first pipe, which is disposed within the hollow cover tube of the first adjustable device, having a first end extended to the steamer spread arm and connected with the outlet. The second pipe, which is disposed within the rotation displacement limiter, having a first end connected to an outlet of the steam generating means. The flexible connecting tube, which is disposed and extended within the first and second turning connectors, being is sealedly connected between a second end of the first pipe and a second end of the second pipe. The supporting spring being disposed within and extended along the connecting tube, in order to support the connecting tube to ensure a fluent steam passage even when the connecting tube is bent.

BRIEF DESCRIPTION OF DRAWINGS

FIG. 1C is a plan view illustrating the second conventional facial steamer operated for a laying patient.

DETAILED DESCRIPTION OF THE PREFERRED EMBODIMENT

Figure 1A:
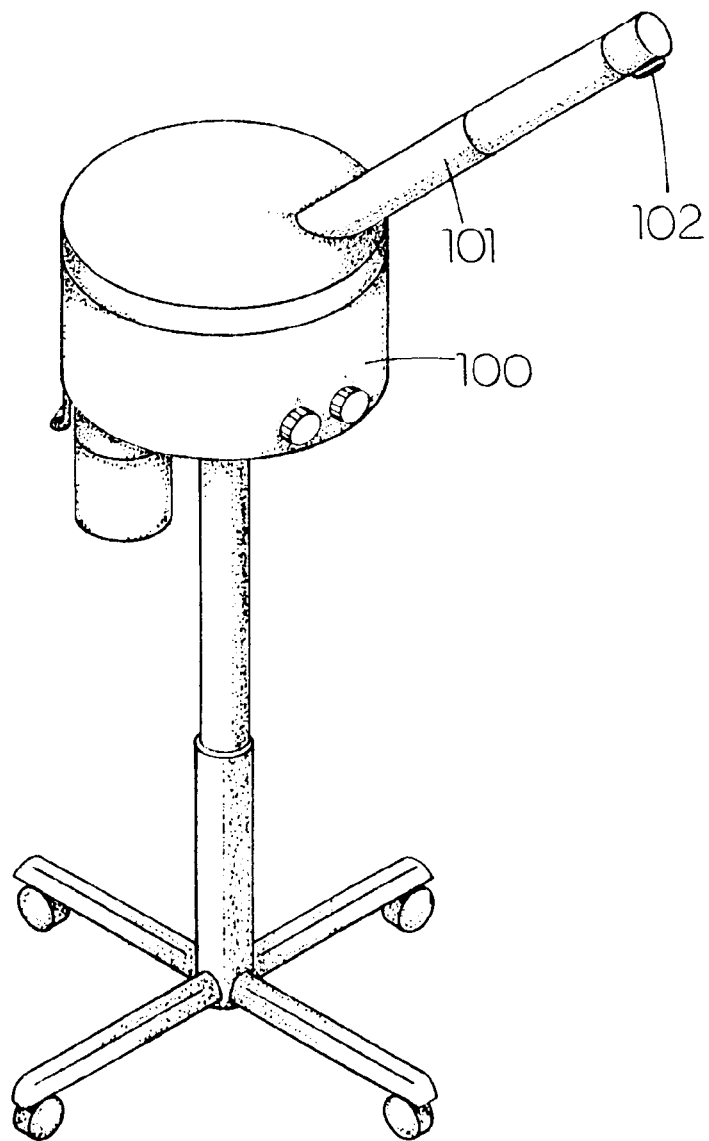
FIG. 1A is a perspective view of a first conventional facial steamer.
Figure 1B:
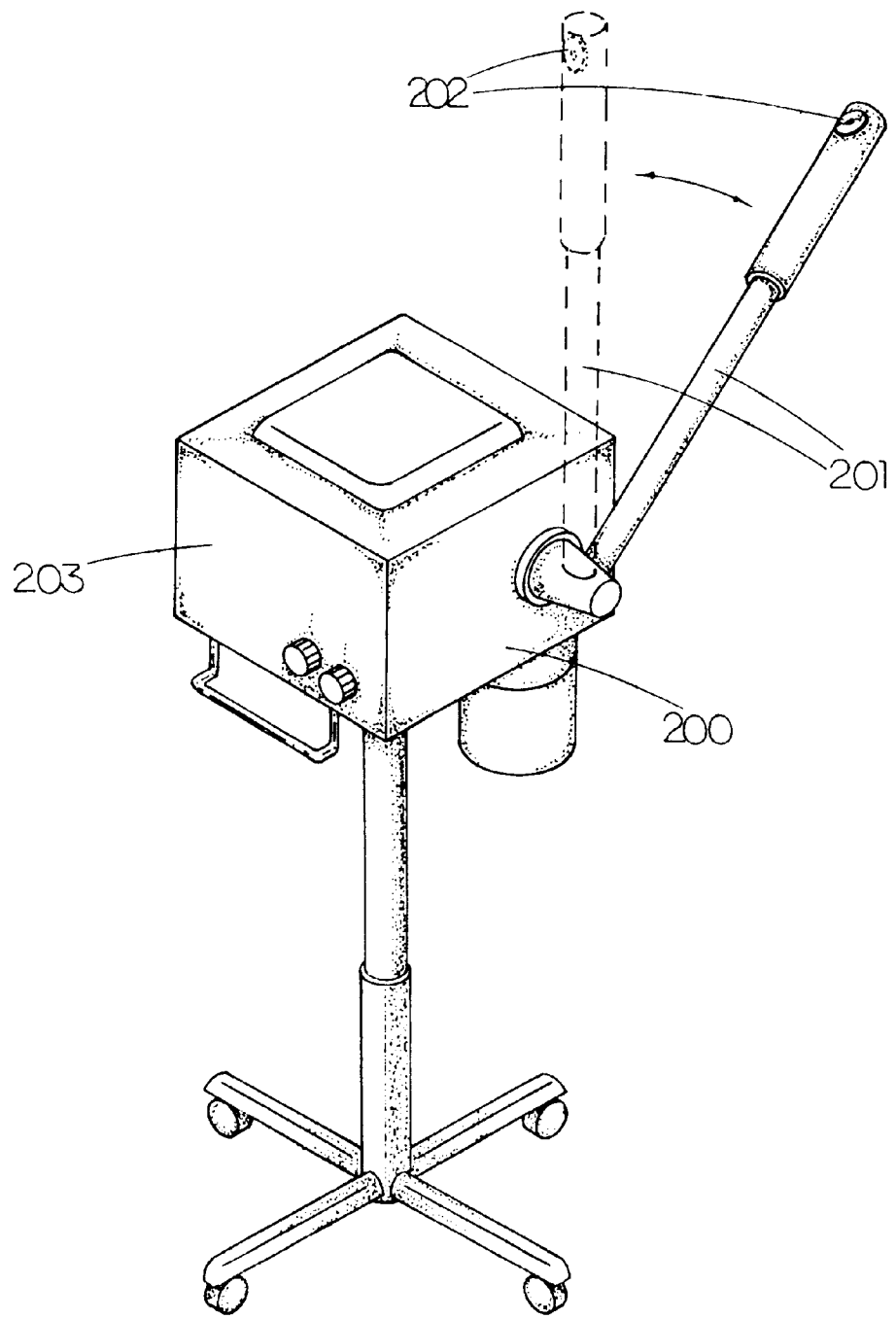
FIG. 1B is a perspective view of a second conventional facial steamer.

Referring to FIG. 2 to FIG. 6 of the drawings, a facial steamer 10 of the present invention comprises a steam generating means 11 for generating steam in a usual manner and an adjustable steamer arm 12 connected to the steam generating means 11. The steam generating means 11 comprises a movable steamer housing 111 having a front operation control panel 112 for controlling the operational functions of the steam generating means 11 and a side connecting plate 113 for mounting the adjustable steamer arm 12 thereto.

The adjustable steamer arm 12 comprises a steamer spread arm 20 having a steam outlet 21 thereon, a first adjustable device 30 connected with the steamer spread arm 20, a second adjustable device 40 hingedly and rotatably connected to the first adjustable device 30 by a first and a second connecting means 50, 60, a steam transporting means 70 for transmitting steam generated from the steam generating means 11 to exit through the steam outlet 21 of the steamer spread arm 20 via the first adjustable device 30 and the second adjustable device 40, and a mounting device 80 installed inside the steamer housing 11 for rotatably mounting the second adjustable device 40 to the side connecting plate 113 of the steam generating means 11.

Figure 3:
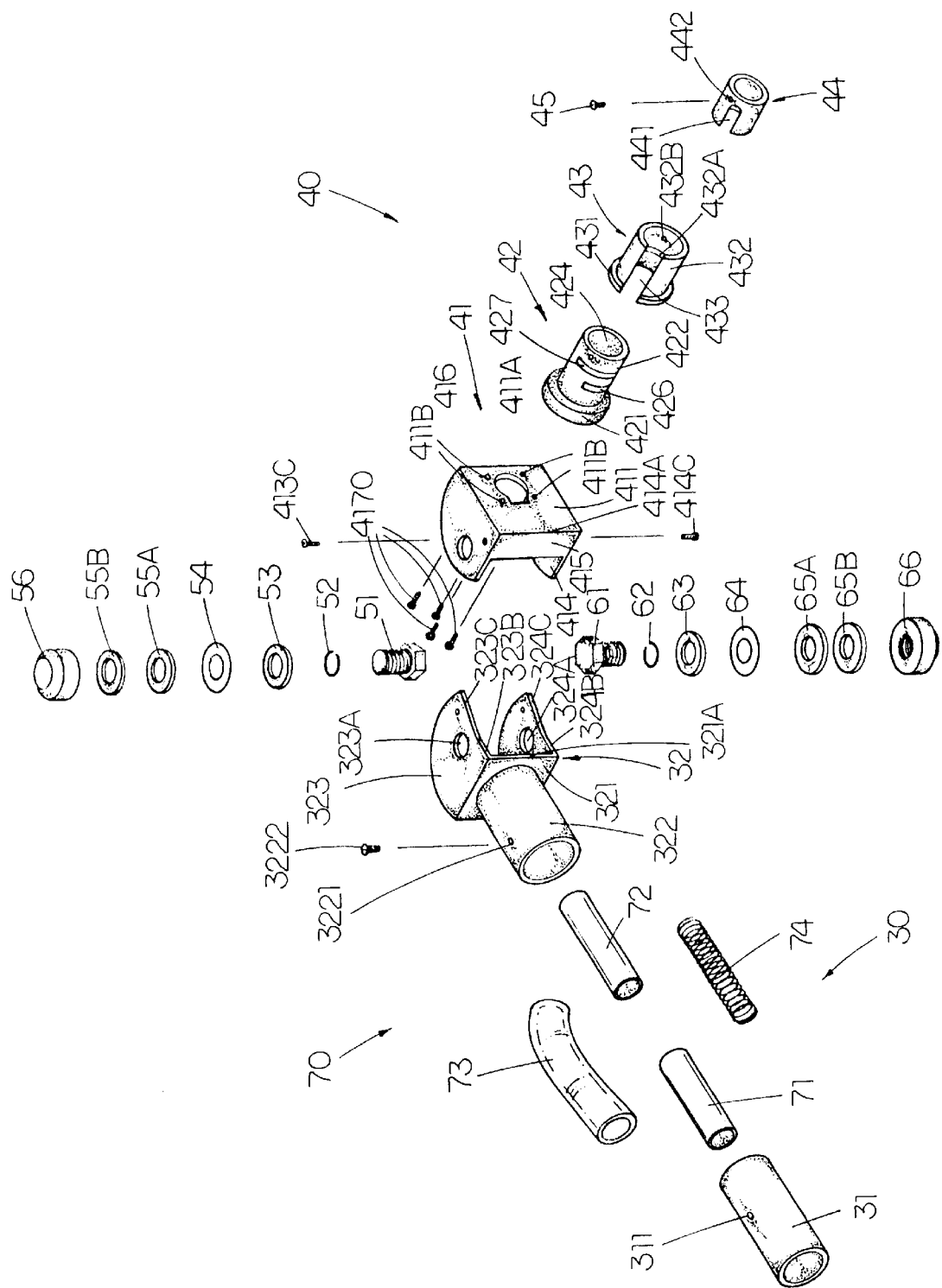
FIG. 3 is an exploded view of the adjustable steamer arm of the facial steamer according to the above preferred embodiment of the present invention.
Figure 4A:
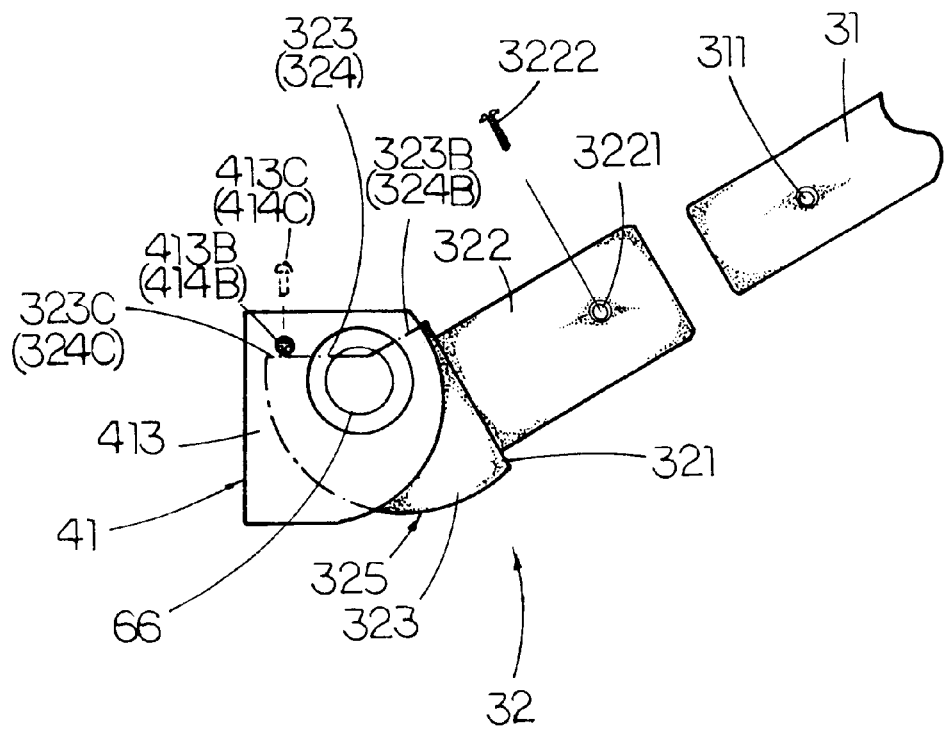
FIG. 4A is a partial exploded view of a front section of an adjustable device of the facial steamer according to the above preferred embodiment of the present invention.
Figure 4B:
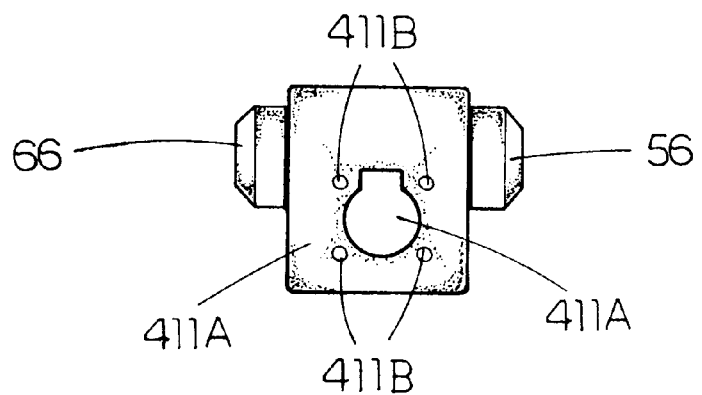
FIG. 4B is a front view of an adjustable base with a locking mean attaches on each side thereof according to the above preferred embodiment of the present invention.
Figure 4C:
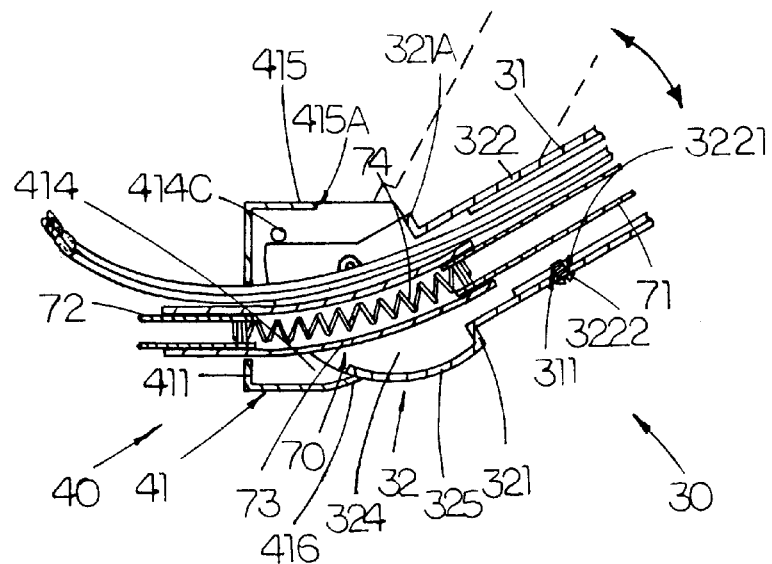
FIG. 4C is a sectional view of the adjustable device of the facial steamer according to the above preferred embodiment of the present invention.
Figure 5:
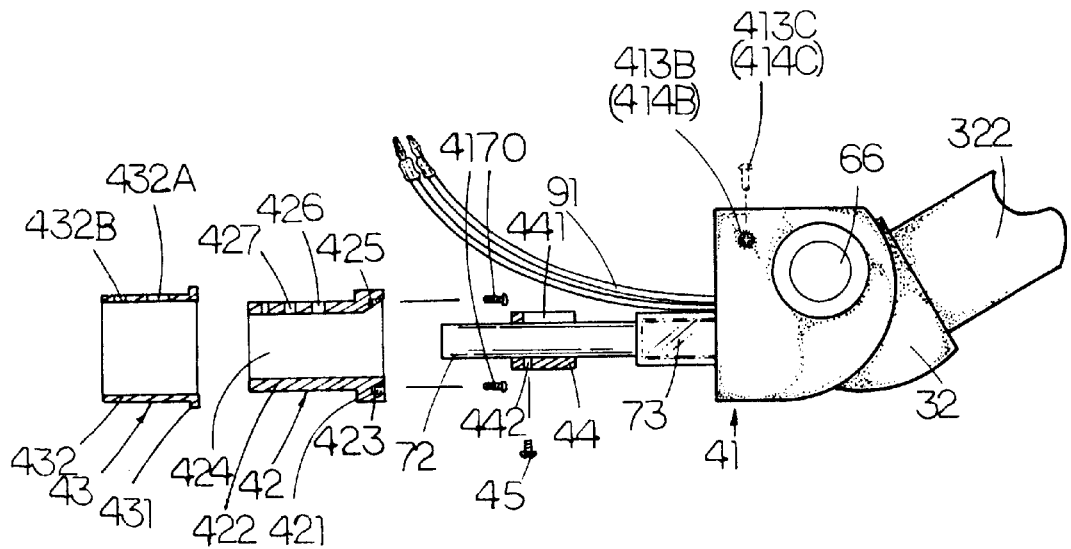
FIG. 5 is a partial exploded view of a back section of the adjustable device of the facial steamer according to the above preferred embodiment of the present invention.

As shown in FIGS. 3 to 5 of the drawings, the adjustable steamer arm 12 of the facial steamer 10 of the present invention is illustrated. The first adjustable device 30 comprises a hollow cover tube 31 with a predetermined diameter and a first turning connector 32. The hollow cover tube 31 has a fixing hole 311 provided on a first end thereof. The second end of the hollow cover tube 31 is connected to the steamer spread are 20.

Referring to FIG. 3, the first turning connector 32 comprises a base wall 321, a circular hollow tube 322 integrally extended from an outer surface of the base wall 321 to connect with the hollow cover tube 31, two symmetrical side walls 323, 324 integrally and parallelly extended from an inner surface of the base wall 321 to form a U-shape body, and a back wall 325 integrally and curvedly extended from the base wall 321 for a predetermined length and transversally connected between the root portions of two first side edges of the two side walls 323, 324 (as shown in FIG. 4C). One of the two parallel side walls 323 has a first hinged hole 323A and the other side wall 324 has a second hinged hole 324A which is coaxially aligned with the first hinged hole 323A.

Each of two second side edges of the two side walls 323, 324 of the first turning connector 32 has a straight root side edge 323B, 324B and an inclined outer edge 323C, 324C, as shown in FIG. 3 and 4A. At the same side of the second side edges of the two side walls 323, 324, the base wall 321 has a locking edge 321A for limiting the turning angle of the first turning connector 32.

Referring to FIGS. 3 and 4A of the drawing, the circular hollow tube 322 of the first turning connector 32 further provides an affixing screw hole 3221 thereon, so that when the circular hollow tube 322 of the first turning connector 32 is inserted into the hollow cover tube 31, a screw 3222 is used to go through the fixing hole 311 of the hollow cover tube 31 and screw to the affixing screw hole 3221 of the circular hollow tube 322 in order to firmly connected the first end of the hollow cover tube 31 with the circular hollow tube 322.

Referring to FIG. 3, the second adjustable device 40 comprises a second turning connector 41, a rotation displacement limiter 42 connected to the second turning connector 41, a friction resistance ring 43 enwrapped the rotation displacement limitor 42, and a metal ring 44.

As shown in FIGS. 3 and 4C, the second turning connector 41 comprises a connecting base wall 411 having an opening 411A thereon and four mounting holes 411B disposed evenly encircling the opening 411A, two symmetrical connecting side walls 413, 414 integrally and parallelly extended from the connecting base wall 411, a front wall 415 integrally extended from the base wall 411 and transversally connected between the roots of two front sides of the two connecting side walls 413, 414, and a rear wall 416 integrally and curvedly extended from the connecting base wall 411 and transversally connected between the roots of two rear sides of the two connecting side walls 413, 414. The front wall 415 has a stopping top edge 415A. One of the two connecting side walls 413 has a first hinging hole 413A and the other connecting side walls 414 has a second hinging hole 414A, in which the first hinging hole 413A is coaxially aligned with the second hinging hole 414A. Each of the connecting side walls 413, 414 further provides a threaded hole 413B, 414B at a predetermined location in the proximity of the front wall 415, so that a threaded stopper 413C, 414C can thus be screwed thereto until penetrating through the connecting side wall 413, 414.

An incorporating relationship between the first turning connector 32 and the second turning connector 41 is that one of which must be smaller than other so that the smaller one can insert its side walls between the side walls of the larger one. According to the present invention, the second turning connector 41 has a size larger than the first turning connector 32. The two side walls 323, 324 of the first turning connector 32 are inserted between the two connecting side walls 413, 414 of the second turning connector 41, wherein one of the two side walls 323 of the first turning connector 32 is pivotally and rotatably connected with one of the connecting side walls 413 of the second turning connector 41 by means of the first connecting means 50, and that the other side wall 324 is pivotally and rotatably connected with the other connecting side wall 414 of the second turning connector 41 by means of the second connecting means 60.

Practically, as shown in FIGS. 3 and 4C, the vertical angle to be allowed to turn by the hollow cover tube 31 is designed to be limited between 0 degrees and 80 degrees, i.e. from a vertical position to a nearly horizontal position. Assume that the first turning connector 32 which represents the Y-axis is perpendicularly positioned in the vertical position with respect to the second turning connector 41 which represents the X-axis as the operation starting point, where the angle therebetween is 90 degrees. Since the locking edge 321A of the base wall 321 of the first turning connector 32 is held against the stopping top edge 415A of the front wall 415 of the second turning connector 41, the first turning connector 32 can be stopped at this vertical position. As the first turning connector 32, i.e. the Y-axis, is allowed to turn down to approximately 80 degrees to a nearly horizontal position, the turning down motion of the first turning connector 32 will be limited when the inclined outer edges 323C, 324C of the two side walls 323, 324 of the first turning connector 32 is stopped by the two stoppers 413C, 414C of the second turning connector 41, wherein the angle between the first turning connector 32 and the second turning connector 41 would then be increased to approximately 170 degrees. The reason of not to allow the first turning connector 32 and the hollow cover tube connected thereto to fully turn down to 90 degree or exceed 90 degree is because the steamer spread arm 20 connected to the hollow cover tube 31 is preferable to be kept in a slightly upwardly inclined position so as to enable the outlet 21 of the steamer spread arm 20 positioning in a highest point of the adjustable steamer arm 12, so that the excessive hot water forms within the steam transporting mean 70 would not drip out of the outlet 21 of the steamer spread arm and burn the skin of the patient laid thereunder.

Referring to FIGS. 3, 4A and 4B of the drawing, the two connecting means 50, 60 comprise two nut bolts 51, 61, two C-ring clips 52, 62, and two washers 53, 63 positioned within the inner surfaces of the two side walls 323, 324 of the first turning connector 32 respectively. The two connecting means 50, 60 further comprises two fiber washers 54, 64 disposed between the outer surfaces of the two side walls 323, 324 of the first turning connector 32 and the inner surfaces of the two connecting side walls 413, 414 of the second turning connector 41 respectively for reducing friction and avoiding overlooking, two pairs of washers 55A, 55B, and 65A, 65B being respectively disposed outside of the outer surfaces of the two connecting side walls 413, 414 of the second turning connector 41, and two locking caps 56, 66 for engaging with the two nut bolts 51, 61 respectively.

The assembling procedure between the first and second connecting means 50, 60, the first turning connector 32 and the second turning connector 41 is recited as follow:

(1) Insert the two side walls 323, 324 of the first turning connector 32 between the two connecting side walls 413, 414 of the second turning connector 41 until the first and second hinged holes 323A, 324A on the two side walls 323, 324 of the first turning connector 32 are aligned coaxially with the first and second hinging holes 413A, 414A of the two connecting side walls 413, 414 of the second turning connector 41. Then position the two fiber washers 54, 64 between the outer surfaces of the two side walls 323, 324 of the first turning connector 32 and the inner surfaces of the two connecting side walls 413 of the second turning connector 41 respectively, wherein the two fiber washers 54, 64 must also be aligned coaxially with the first and second hinged holes 323A, 324A and the first and second hinging holes 413A, 414A.

(2) Insert the two C-ring clips 52, 62 and the two washers 53, 63 through the two nut bolts 51, 61 respectively.

(3) Pass the two nut bolts 51, 61 each having the corresponding C-ring clip 52, 62 and the corresponding washer 53, 63 through the first and second hinged holes 323A, 324A of the two side walls 323, 324 of the first turning connector 32, the two fiber washers 54, and the first and second hinging holes 413A, 414A of the two side walls 413, 414 of the second turning connector 41 respectively.

(4) Insert the two pairs of washers 55A, 55B and 65A, 65B through the two nut bolts 51, 61 and tighten the two locking caps 56, 66 on two tips of the two nut bolts 51, 61 respectively, so that the first turning connector 32 and the second turning connector 41 are pivotally connected with together.

As shown in FIGS. 3, 4B, and 5, the rotation displacement limitor 42 comprises an enlarged heading rim portion 421 having four evenly spaced threaded fastening holes 423 provided on a top surface thereof for affixing to connecting base wall 411 of the second turning connector 41 by secrewing four screws 4170 to the four threaded fastening holes 423 through the four mounting holes 411 B on the connecting base wall 411. The rotation displacement limiter 42 further has a tubular body portion 422 integrally extended downwardly from the heading rim portion 421, so that a through hole chamber 424 is defined within the body portion 422 for enabling a plurality of electrical wires 91 to pass through.

The electrical wires 91 are extended from the steam generating means 11 through the adjustable steam arm 20 to provide electricity to any electrical appliance such as lighting device installed inside the steamer spread arm 12. The top surface of the heading rim portion 421 further provides an inclined indention 425 to enable the plurality of electrical wires 91 passing through for guiding the extending of the plurality of electrical wires 91 and preventing them from getting unexpected entangled.

The body portion 422 has a first elongated slot 426 circumferentially provided on the surface of the body portion 422, and a second elongated slot 427 offsetly and circumferential provided on the surface of the body portion 422, wherein the first elongated slot 426 is parallel to the second elongated slot 427. The length and the width of the first elongated slot 426 and the second elongated slot 427 disposed on the surface of the body portion 422 are identical, except that a starting point and an ending point of the second elongated slot 427 is offset from the starting point and the ending point of the first elongated slot 426 respectively.

The friction resistance ring 43 is made of plastic material which comprises a head rim 431 and a hollow ring body 432 extended from the head rim 431. The head rim 431 is pushed up against the heading rim portion 421 of the rotation displacement limitor 42 while the friction resistance ring 43 is installed between the rotation displacement limitor 42 and the mounting device 80, wherein the ring body 432 has a diameter slightly larger than a diameter of the body portion 422 of the rotation displacement limitor 42, so that the friction resistance ring 43 is able to slip up the rotation displacement limiter 42.

The ring body 432 of the friction resistance ring 43 also has a first elongated through slot 432A provided thereon with respect to a location of the first elongated slot 426 of the rotation displacement limitor 42. A side locking hole 432B is provided on the body portion 432 of the friction resistance ring 43 with respect to a location of the second elongated slot 427 of the rotation displacement limiter 42. Along the friction resistance ring 43, a longitudinal gap 433 is cut therethrough for more flexible installation.

As shown in FIG. 3 and FIG. 4C, the steam transporting mean 70 of the present invention comprises a copper made first pipe 71, a copper made second pipe 72, a heat resistant plastic-made flexible connecting tube 73, and a stainless supporting spring 74. The first pipe 71, which is disposed within the hollow cover tube 31 of the first adjustable device 30, has a first end extended to the steamer spread arm 20 and connected with the outlet 21. The second pipe 72, having shorter length, is disposed within the rotation displacement limiter 42 and has a first end connected to an outlet of the steam generating means 11 of the facial steamer 10. The flexible connecting tube 73, which is disposed and extended within the first and second turning connectors 32, 41, is sealedly connected between a second end of the first pipe 71 and a second end of the second pipe 72. The supporting spring 74 is disposed within and extended along the connecting tube 73, wherein the supporting spring 74 has a specific duty to support the connecting tube 73 so as to ensure a fluent steam passage even when the connecting tube 73 is bent for 90 degrees or more. Therefore, even though the first turning connector 32 is folded perpendicularly with the second turning connector 41 and the connecting tube 73 is bent accordingly, the supporting spring 74 can still retain a fluent steam passage inside the connecting tube 73 and thus the steam can pass therethrough.

Figure 6:
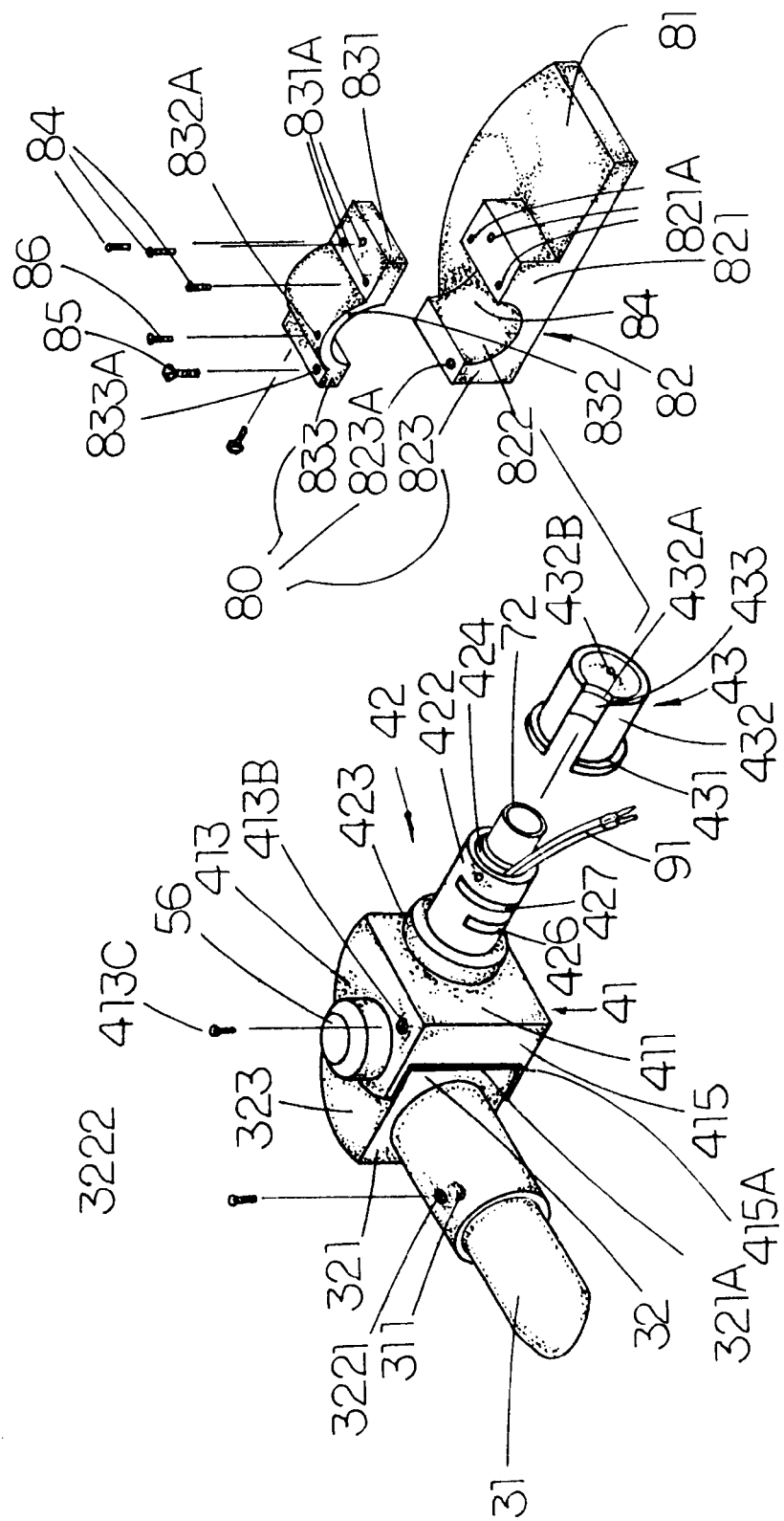
FIG. 6 is an exploded partial perspective view of the adjustable steamer arm in connection with a mounting device of the facial steamer according to the above preferred embodiment of the present invention.

According to FIGS. 3 and 6 of the drawings, the metal ring 44 of the second adjustable device 40 has an indention 441 and a screw hole 442 thereon, wherein the indention 441 is designed for further limiting the extending of the plurality of electrical wires 91 and further preventing the electrical wires 91 from getting entangled. The metal ring is enwrapped around the second pipe 72, and that a screw 45 is screwed through the screw hole 442 until the screw 45 is pressed on the second pipe 72 in order to affixed the metal ring 44 in position. The metal ring also has another purpose of fixing the length of the second pipe 72 which will be allowed to insert into the steam outlet of the steam generating means 11 of the facial steamer 10.

The mounting device 80 comprises a main plate 81, a C-shape bottom half mounting stand 82 integrally extended from an edge of the main plate 81, and a C-shape top half mounting stand 83 which is constructed in mirror image of the C-shaped bottom half mounting stand 82. By affixing the C-shaped top half mounting stand 83 on the C-shaped bottom half mounting stand 82, a circular passage 84 is formed therebetween for holding and mounting the rotation displacement limitor 42 with the friction resistance ring 43 therein.

The C-shaped top half mounting stand 83 comprises a right wing 831, a semi-circular central portion 832 having one end integrally connect to the right wing 831, and a left wing 833 integrally connect to the another end of the central portion 832. According to the present invention, the right wing 83 1 of the C-shaped top half mounting stand 83 has three fastening holes 831 A; the central portion 832 has a central limiting hole 832A; and the left wing 833 has a bolt hole 833A and a side limiting hole 833B.

The C-shaped bottom half mounting stand 82 comprises a right wing 821, a semi-circular central indenting portion 822 integrally connect to the right wing 821, and a left wing 823 integrally connect to the central indenting portion 822. According to the present invention, the right wing 821 of the C-shaped bottom half mounting stand 82 has three fastening screw holes 821 A, and the left wing 823 has a bolting hole 823A.

The C-shaped top half mounting stand 83 is connected to the C-shaped bottom half mounting stand 82 by three screws 84 passing through the three fastening holes 83 1A of the C-shaped top half mounting stand 83 and screwing into the three fastening screw holes 821A of the C-shaped bottom half mounting stand 82. There is also a bolt 85 screw through the bolt hole 833A of the left wing of the C-shaped top half mounting stand 83 and the bolting hole 823A of the left wing of the C-shaped bottom half mounting stand 82.

The rotation displacement of the adjustable steamer arm 12 is limited by the rotation displacement limitor 42, in which a vertical limiting screw 86 is screwed through the central limiting hole 832A and passed through the first elongated slot 426 of the rotation displacement limitor 42, and that a horizontal limiting screw 87 is screwed through the side limiting hole and passed through the second elongated slot 427 of the rotation displacement limiter 42. As the rotation displacement limitor 42 is rotating, the whole adjustable steamer arm 12 would rotate at same distance. The length of the first and second elongated slots 426, 427 is the limiting factor on how much the adjustable steamer arm 12 can be rotated.

Accordingly, the adjustable steamer arm 20 of the present invention can be adapted to be selectively rotated along an connecting axis thereof and swung up and down for enabling the cosmetician to selectively adjust the adjustable steamer arm 20 to an adequate position with respect to the face position of the patient more easier.

Figure 2:
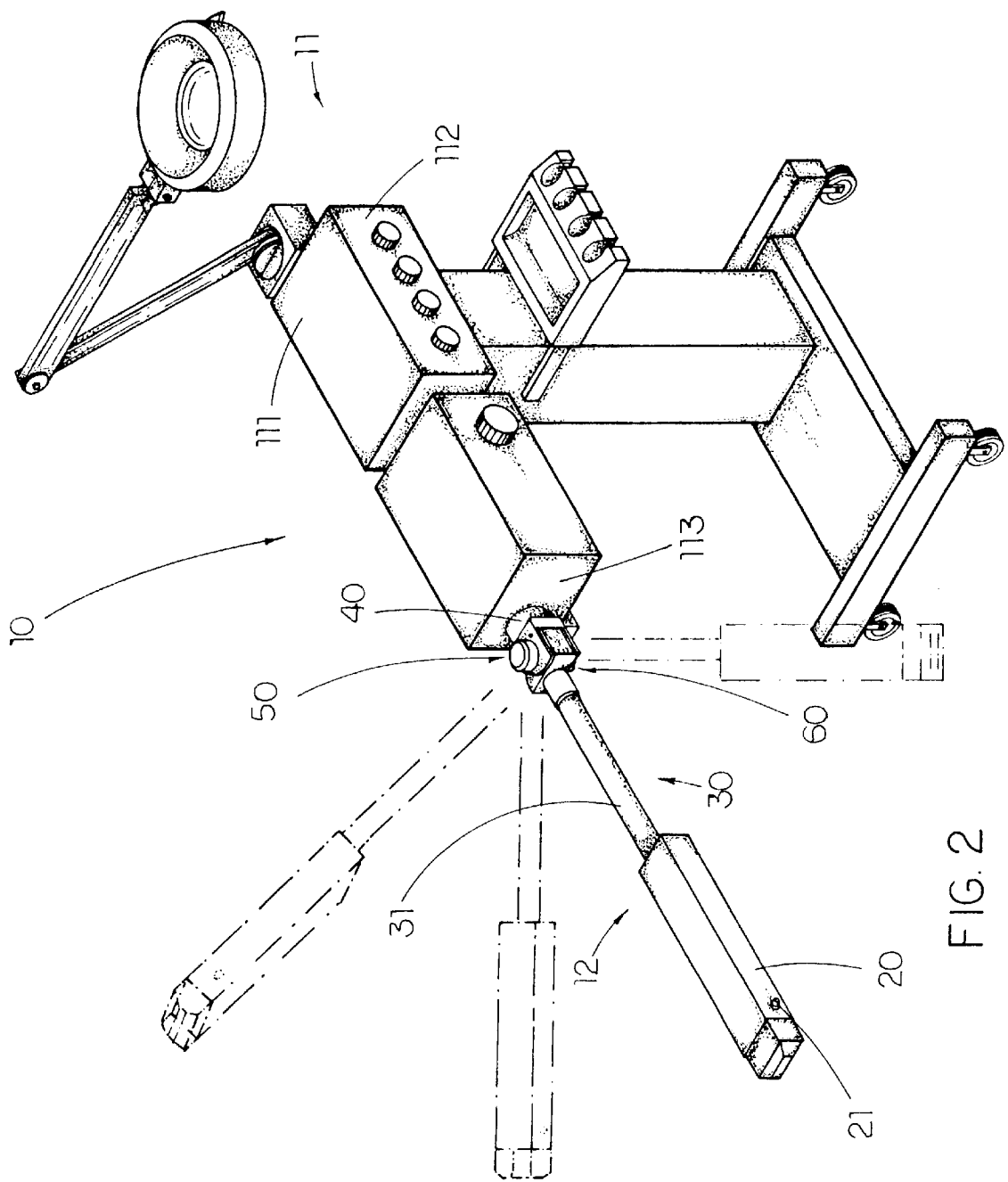
FIG. 2 is a perspective view of a facial steamer with an adjustable steamer arm according to a preferred embodiment of the present invention.

Moreover, due to the flexibility of the adjustable steamer arm 20 of the present invention, the facial steamer 10 is able to be located at a hand reaching position closely to the cosmetician for ensuring easy operation, wherein the operation control panel 112 is provided on a front side of the facial steamer 10, as shown in FIG. 2, that is the closest position Besides, the steam outlet 21 of the adjustable steamer arm 20 can be rotated by rotating the adjustable steamer arm 20 within a wide angle between an upper position and a lower position in order to adapt for various steam applying angles and purposes to fulfill different patients' need.

In addition, the steam transmitting means 70 of the adjustable steamer arm 20 of the present invention ensures a fluent passage for the steam generated from the steamer device even when the adjustable steamer arm 20 is swung to bend. Furthermore, the rotating angle of the adjustable steamer arm 20 is operationally limited by the rotation displacement limiter 42 to prevent the electrical wires 91 extending from the steam generating means 11 to the adjustable steamer arm 20 being tangled up.

I claim:

1. A facial steamer, comprising:

a steam generating means for generating steam and an adjustable steamer arm connected to said steam generating means, said steam generating means comprising a movable steamer housing having a front operation control panel for controlling a plurality of operational functions of said steam generating means and a side connecting plate for mounting said adjustable steamer arm thereto;

said adjustable steamer arm comprising a steamer spread arm having a steam outlet thereon, a first adjustable device connected with said steamer spread arm, a second adjustable device hingedly and rotatably connected to said first adjustable device by a first and a second connecting means, a steam transporting means for transmitting steam generated from said steam generating means to exit through said steam outlet of said steamer spread arm via said first adjustable device and said second adjustable device, and a mounting device installed inside said steamer housing for rotatably mounting said second adjustable device to said side connecting plate of said steam generating means;

said first adjustable device comprising a hollow cover tube with a predetermined diameter and a first turning connector, said hollow cover tube having a first end connected to said first turning connector and a second end connected to said steamer spread arm;

said second adjustable device comprising a second turning connector which is rotatably and hingedly connected with said first turning connector, a rotation displacement limiter for rotatably connecting said second turning connector to said mounting device and limiting a rotation angle of said second turning connector with respect to said mounting device, and a friction resistance ring enwrapping said rotation displacement limiter for reducing friction therebetween; so that said first adjustable device is able to swing up and down with respect to said second adjustable device, and that said second adjustable device is able to rotate with respect to said steam generating means;

said steam transporting mean comprising a first pipe, a second pipe, a heat resistant flexible connecting tube, and a supporting spring;

said first pipe, which is disposed within said hollow cover tube of said first adjustable device, having a first end extended to said steamer spread arm and connected with said outlet;

said second pipe, which is disposed within said rotation displacement limiter, having a first end connected to an outlet of said steam generating means;

said flexible connecting tube, which is disposed and extended within said first and second turning connectors, being sealedly connected between a second end of said first pipe and a second end of said second pipe; and said supporting spring being disposed within and extended along said connecting tube, in order to support said connecting tube to ensure a fluent steam passage even when said connecting tube is bent.

2. A facial steamer, as recited in claim 1, wherein said first turning connector comprises a base wall, a circular hollow tube integrally extended from an outer surface of said base wall to connect with said hollow cover tube, two symmetrical side walls integrally and parallelly extended from an inner surface of said base wall to form a U-shape body, one of said two parallel side walls having a first hinged hole and said other side wall having a second hinged hole which is coaxially aligned with said first hinged hole, at a same side of side edges of said two parallel side walls, said base wall having a locking edge for limiting a turning angle of said first turning connector, wherein said circular hollow tube of said first turning connector is inserted into and connected to said hollow cover tube, said second turning connector comprising a connecting base wall having an opening thereon and a plurality of mounting holes disposed evenly encircling said opening, two symmetrical connecting side walls integrally and parallelly extended from said connecting base wall, a front wall integrally extended from said base wall and transversally connected between roots of two front sides of said two connecting side wall, said front wall having a stopping top edge, one of said two connecting side walls having a first hinged hole and said other connecting side walls having a second hinged hole, wherein said first hinging hole is coaxially aligned with said second hinged hole.

3. A facial steamer, as recited in claim 2, wherein said second turning connector has a size larger than said first turning connector, said two side walls of said first turning connector being inserted between said two connecting side walls of said second turning connector, one of said two side walls of said first turning connector being pivotally and rotatably connected with one of said connecting side walls of said second turning connector by said first connecting means, and that said other side wall of said first turning connector is pivotally and rotatably connected with said other connecting side wall of said second turning connector by said second connecting means.

4. A facial steamer, as recited in claim 3, wherein at least one of said connecting side walls further provides a stopper extended inwardly at a predetermined location in said proximity of said front wall, each of two side edges of said two side walls of said first turning connector having a straight root side edge and an inclined outer edge, so that a vertical angle allowed to turn by said first adjustable device is limited within an turning angle less than 90 degrees, wherein since said locking edge of said base wall of said first turning connector is held against said stopping top edge of said front wall of said second turning connector, an upwardly turning of said first turning connector is stopped at a vertical position, and that as said first turning connector is allowed to turn down to a nearly horizontal position, said turning down motion of said first turning connector is limited when said inclined outer edges of said two side walls of said first turning connector is stopped by said stopper of said second turning connector.

5. A facial steamer, as recited in claim 3, wherein said two connecting means comprise two bolts with nuts, two C-ring clips, two washers positioned within inner surfaces of said two side walls of said first turning connector respectively, two fiber washers disposed between outer surfaces of said two side walls of said first turning connector and said inner surfaces of said two connecting side walls of said second turning connector respectively for reducing friction and avoiding overlooking, two pairs of washers being respectively disposed outside of said outer surfaces of said two connecting side walls of said second turning connector, and two locking caps for engaging with said two nut bolts respectively, wherein said two side walls of said first turning connector are inserted between said two connecting side walls of said second turning connector until said first and second hinged holes on said two side walls of said first turning connector are aligned coaxially with said first and second hinged holes of said two connecting side walls of said second turning connector, said two fiber washers being positioned between said outer surfaces of said two side walls of said first turning connector and said inner surfaces of said two connecting side walls of said second turning connector respectively, said two fiber washers being aligned coaxially with said first and second hinged holes and said first and second hinging holes, said two C-ring clips and said two washers being inserted through said two bolts with nuts respectively, said two nut bolts each having said corresponding C-ring clip and said corresponding washer thereon being passed through said first and second hinged holes of said two side walls of said first turning connector, said two fiber washers, and said first and second hinging holes of said two side walls of said second turning connector respectively, said two pairs of washers being inserted through said two bolts with nuts and said two locking caps being tightened on two tips of said two bolts with nuts respectively, so that said first turning connector and said second turning connector are pivotally connected together.

6. A facial steamer, as recited in claim 4, wherein said two connecting means comprise two nut bolts, two C-ring clips, two washers positioned within inner surfaces of said two side walls of said first turning connector respectively, two fiber washers disposed between outer surfaces of said two side walls of said first turning connector and said inner surfaces of said two connecting side walls of said second turning connector respectively for reducing friction and avoiding overlooking, two pairs of washers being respectively disposed outside of said outer surfaces of said two connecting side walls of said second turning connector, and two locking caps for engaging with said two nut bolts respectively, wherein said two side walls of said first turning connector are inserted between said two connecting side walls of said second turning connector until said first and second hinged holes on said two side walls of said first turning connector are aligned coaxially with said first and second hinging holes of said two connecting side walls of said second turning connector, said two fiber washers being positioned between said outer surfaces of said two side walls of said first turning connector and said inner surfaces of said two connecting side walls of said second turning connector respectively, said two fiber washers being aligned coaxially with said first and second hinged holes and said first and second hinging holes, said two C-ring clips and said two washers being inserted through said two nut bolts respectively, said two nut bolts each having said corresponding C-ring clip and said corresponding washer thereon being passed through said first and second hinged holes of said two side walls of said first turning connector, said two fiber washers, and said first and second hinged holes of said two side walls of said second turning connector respectively, said two pairs of washers being inserted through said two nut bolts and said two locking caps being tightened on two tips of said two nut bolts respectively, so that said first turning connector and said second turning connector are pivotally connected with together.

7. A facial steamer, as recited in claim 1, wherein said rotation displacement limiter comprises an enlarged heading rim portion affixed to said connecting base wall of said second turning connector, said rotation displacement limiter further having a tubular body portion integrally extended downwardly from said heading rim portion, so that a through hole chamber is defined within said body portion, said body portion having a first elongated slot circumferentially provided on a circumferential surface of said body portion, and a second elongated slot offset on said circumferential surface of said body portion, wherein said first elongated slot is parallel to said second elongated slot, wherein a length and a width of said first elongated slot are identical to that of said second elongated slot, that is a starting point and an ending point of said second elongated slot is offset from a starting point and an ending point of said first elongated slot respectively, said friction resistance ring comprising a head rim and a hollow ring body extended from said head rim, said head rim being pushed up against said heading rim portion of said rotation displacement limiter while said friction resistance ring is installed between said rotation displacement limiter and said mounting device, wherein said ring body has a diameter slightly larger than a diameter of said body portion of said rotation displacement limiter, so that said friction resistance ring is able to slip up said rotation displacement limiter, said ring body of said friction resistance ring also having a first elongated through slot provided thereon with respect to a location of said first elongated slot of said rotation displacement limiter, a side locking hole being provided on said body portion of said friction resistance ring with respect to a location of said second elongated slot of said rotation displacement limiter.

8. A facial steamer, as recited in claim 3, wherein said rotation displacement limiter comprises an enlarged heading rim portion having a plurality of evenly spaced threaded fastening holes provided on a top surface thereof for affixing to said connecting base wall of said second turning connector by screwing a plurality of screws to said four threaded fastening holes through said plurality of mounting holes on said connecting base wall, said rotation displacement limiter further having a tubular body portion integrally extended downwardly from said heading rim portion, so that a through hole chamber is defined within said body portion, said body portion having a first elongated slot circumferentially provided on a circumferential surface of said body portion, and a second elongated slot offset on said circumferential surface of said body portion, wherein said first elongated slot is parallel to said second elongated slot, wherein a length and a width of said first elongated slot are identical to that of said second elongated slot, that is a starting point and an ending point of said second elongated slot is offset from a starting point and an ending point of said first elongated slot respectively, said friction resistance ring comprising a head rim and a hollow ring body extended from said head rim, said head rim being pushed up against said heading rim portion of said rotation displacement limiter while said friction resistance ring is installed between said rotation displacement limiter and said mounting device, wherein said ring body has a diameter slightly larger than a diameter of said body portion of said rotation displacement limiter, so that said friction resistance ring is able to slip up said rotation displacement limiter, said ring body of said friction resistance ring also having a first elongated through slot provided thereon with respect to a location of said first elongated slot of said rotation displacement limiter, a side locking hole being provided on said body portion of said friction resistance ring with respect to a location of said second elongated slot of said rotation displacement limiter.

9. A facial steamer, as recited in claim 4, wherein said rotation displacement limiter comprises an enlarged heading rim portion having a plurality of evenly spaced threaded fastening holes provided on a top surface thereof for affixing to said connecting base wall of said second turning connector by screwing a plurality of screws to said four threaded fastening holes through said plurality of mounting holes on said connecting base wall, said rotation displacement limiter further having a tubular body portion integrally extended downwardly from said heading rim portion, so that a through hole chamber is defined within said body portion, said body portion having a first elongated slot circumferentially provided on a circumferential surface of said body portion, and a second elongated slot offset on said circumferential surface of said body portion, wherein said first elongated slot is parallel to said second elongated slot, wherein a length and a width of said first elongated slot are identical to that of said second elongated slot, that is a starting point and an ending point of said second elongated slot is offset from a starting point and an ending point of said first elongated slot respectively, said friction resistance ring comprising a head rim and a hollow ring body extended from said head rim, said head rim being pushed up against said heading rim portion of said rotation displacement limiter while said friction resistance ring is installed between said rotation displacements limiter and said sounting device, wherein said ring body has a diameter slightly larger than a diameter of said body portion of said rotation displacement limiter, so that said friction resistance ring is able to slip up said rotation displaement limiter, said ring body of said friction resistance ring also having a first elongated through slot provided thereon with respect to a location of said first elongated slot of said rotation displacement limiter, a side locking hole being provided on said body portion of said friction resistance ring with respect to a location of said second elongated slot of said rotation displacement limiter.

10. A facial steamer, as recited in claim 5, wherein said rotation displacement Iimiter comprises an enlarged heading rim portion having a plurality of evenly spaced threaded fastening holes provided on a top Surface thereof for affixing to said connecting base wall of said second turning connector by screwing a plurality of screws to said four threaded fastening holes through said plurality of mounting holes on said connecting base wall, said rotation displacement limiter further having a tubular body portion integrally extended downwardly from said heading rim portion, so that a through hole chamber is defined within said body portion, said body portion having a first elongated slot circumferentially provided on a circumferential surface of said body portion, and a second elongated slot offset on said circumferential surface of said body portion, wherein said first elongated slot is parallel to said second elongated slot, wherein a length and a width of said first elongated slot are identical to that of said second elongated slot, that is a starting point and an ending point of said second elongated slot is offset from a starting point and an ending point of said first elongated slot respectively, said friction resistance ring comprising a head rim and a hollow ring body extended from said head rim, said head rim being pushed up against said heading rim portion of said rotation displacement limiter while said friction resistance ring is installed between said rotation displacement limiter and said mounting device, wherein said ring body has a diameter slightly larger than a diameter of said body portion of said rotation displacement limiter, so that said friction resistance ring is able to slip up said rotation displacement limiter, said ring body of said friction resistance ring also having a first elongated through slot provided thereon with respect to a location of said first elongated slot of said rotation displacement limiter, a side locking hole being provided on said body portion of said friction resistance ring with respect to a location of said second elongated slot of said rotation displacement limiter.

11. A facial steamer, as recited in claim 6, wherein said rotation displacement limiter comprises an enlarged heading rim portion having a plurality of evenly spaced threaded fastening holes provided on a top surface thereof for affixing to said connecting base wall of said second turning connector by screwing a plurality of screws to said four threaded fastening holes through said plurality of mounting holes on said connecting base wall, said rotation displacement limiter further having a tubular body portion integrally extended downwardly from said heading rim portion, so that a through hole chamber is defined within said body portion, said body portion having a first elongated slot circumferentially provided on a circumferential surface of said body portion, and a second elongated slot offset on said circumferential surface of said body portion, wherein said first elongated slot is parallel to said second elongated slot, wherein a length and a width of said first elongated slot are identical to that of said second elongated slot, that is a starting point and an ending point of said second elongated slot is offset from a starting point and an ending point of said first elongated slot respectively, said friction resistance ring comprising a head rim and a hollow ring body extended from said head rim, said head rim being pushed up against said heading rim portion of said rotation displacement limiter while said friction resistance ring is installed between said rotation displacement limiter and said mounting device, wherein said ring body has a diameter slightly larger than a diameter of said body portion of said rotation displacement limiter, so that said friction resistance ring is able to slip up said rotation displacement limiter, said ring body of said friction resistance ring also having a first elongated through slot provided thereon with respect to a location of said first elongated slot of said rotation displacement limiter, a side locking hole being provided on said body portion of said friction resistance ring with respect to a location of said second elongated slot of said rotation displacement limiter.

12. A facial steamer, as recited in claim 1, wherein said mounting device comprises a main plate, a C-shape bottom half mounting stand integrally extended from an edge of said main plate, and a C-shape top half mounting stand, wherein by affixing said C-shaped top half mounting stand on said C-shaped bottom half mounting stand, a circular passage is formed therebetween for holding and mounting said rotation displacement limiter with said friction resistance ring therein.

13. A facial steamer, as recited in claim 7, wherein said mounting device comprises a main plate, a C-shape bottom half mounting stand integrally extended from an edge of said main plate, and a C-shape top half mounting stand, wherein by affixing said C-shaped top half mounting stand on said C-shaped bottom half mounting stand, a circular passage is formed therebetween for holding and mounting said rotation displacement limiter with said friction resistance ring therein.

14. A facial steamer, as recited in claim 13, wherein said C-shaped top half mounting stand comprises a right wing, a semi-circular central portion having one end integrally connect to said right wing, and a left wing integrally connect to said another end of said central portion, said right wing of said C-shaped top half mounting stand having a plurality of fastening holes, said central portion having a central limiting hole, said left wing having a bolt hole and a side limiting hole, said C-shaped bottom half mounting stand comprising a right wing, a semi-circular central indenting portion integrally connect to said right wing, and a left wing integrally connecting to said central indenting portion, said right wing of said C-shaped bottom half mounting stand having a plurality of fastening screw holes, and said left wing having a bolting hole, wherein said C-shaped top half mounting stand being connected to said C-shaped bottom half mounting stand by a plurality of screws passing through said plurality of fastening holes of said C-shaped top half mounting stand and screwing into said plurality of fastening screw holes of said C-shaped bottom half mounting stand, a bolt being screwed through said bolt hole of said left wing of said C-shaped top half mounting stand and said bolting hole of said left wing of said C-shaped bottom half mounting stand, so that said rotation displacement of said adjustable steamer arm is limited by said rotation displacement limiter, in which a vertical limiting screw is screwed through said central limiting hole and passed through said first elongated slot of said rotation displacement limiter, and that a horizontal limiting screw is screwed through said side limiting hole and passed through said second elongated slot of said rotation displacement limiter, therefore as said rotation displacement limiter is rotating, said adjustable steamer arm is rotated at a same distance.

15. A facial steamer, as recited in claim 8, wherein said mounting device comprises a main plate, a C-shape bottom half mounting stand integrally extended from an edge of said main plate, and a C-shape top half mounting stand, wherein by affixing said C-shaped top half mounting stand on said C-shaped bottom half mounting stand, a circular passage is formed therebetween for holding and mounting said rotation displacement limiter with said friction resistance ring therein, wherein said C-shaped top half mounting stand comprises a right wing, a semi-circular central portion having one end integrally connect to said right wing, and a left wing integrally connect to said another end of said central portion, said right wing of said C-shaped top half mounting stand having a plurality of fastening holes, said central portion having a central limiting hole, said left wing having a bolt hole and a side limiting hole, said C-shaped bottom half mounting stand comprising a right wing, a semi-circular central indenting portion integrally connect to said right wing, and a left wing integrally connecting to said central indenting portion, said right wing of said C-shaped bottom half mounting stand having a plurality of fastening screw holes, and said left wing having a bolting hole, wherein said C-shaped top half mounting stand being connected to said C-shaped bottom half mounting stand by a plurality of screws passing through said plurality of fastening holes of said C-shaped top half mounting stand and screwing into said plurality of fastening screw holes of said C-shaped bottom half mounting stand, a bolt being screwed through said bolt hole of said left wing of said C-shaped top half mounting stand and said bolting hole of said left wing of said C-shaped bottom half mounting stand, so that said rotation displacement of said adjustable steamer arm is limited by said rotation displacement limiter, in which a vertical limiting screw is screwed through said central limiting hole and passed through said first elongated slot of said rotation displacement limiter, and that a horizontal limiting screw is screwed through said side limiting hole and passed through said second elongated slot of said rotation displacement limiter, therefore as said rotation displacement limiter is rotating, said adjustable steamer arm is rotated at a same distance.

16. A facial steamer, as recited in claim 9, wherein said mounting device comprises a main plate, a C-shape bottom half mounting stand integrally extended from an edge of said main plate, and a C-shape top half mounting stand, wherein by affixing said C-shaped top half mounting stand on said C-shaped bottom half mounting stand, a circular passage is formed therebetween for holding and mounting said rotation displacement limiter with said friction resistance ring therein, wherein said C-shaped top half mounting stand comprises a right wing, a semi-circular central portion having one end integrally connect to said right wing, and a left wing integrally connect to said another end of said central portion, said right wing of said C-shaped top half mounting stand having a plurality of fastening holes, said central portion having a central limiting hole, said left wing having a bolt hole and a side limiting hole, said C-shaped bottom half mounting stand comprising a right wing, a semi-circular central indenting portion integrally connect to said right wing, and a left wing integrally connecting to said central indenting portion, said right wing of said C-shaped bottom half mounting stand having a plurality of fastening screw holes, and said left wing having a bolting hole, wherein said C-shaped top half mounting stand being connected to said C-shaped bottom half mounting stand by a plurality of screws passing through said plurality of fastening holes of said C-shaped top half mounting stand and screwing into said plurality of fastening screw holes of said C-shaped bottom half mounting stand, a bolt being screwed through said bolt hole of said left wing of said C-shaped top half mounting stand and said bolting hole of said left wing of said C-shaped bottom half mounting stand, so that said rotation displacement of said adjustable steamer arm is limited by said rotation displacement limiter, in which a vertical limiting screw is screwed through said central limiting hole and passed through said first elongated slot of said rotation displacement limiter, and that a horizontal limiting screw is screwed through said side limiting hole and passed through said second elongated slot of said rotation displacement limiter, therefore as said rotation displacement limiter is rotating, said adjustable steamer arm is rotated at a same distance.

17. A facial steamer, as recited in claim 10, wherein said mounting device comprises a main plate, a C-shape bottom half mounting stand integrally extended from an edge of said main plate, and a C-shape top half mounting stand, wherein by affixing said C-shaped top half mounting stand on said C-shaped bottom half mounting stand, a circular passage is formed therebetween for holding and mounting said rotation displacement limiter with said friction resistance ring therein, wherein said C-shaped top half mounting stand comprises a right wing, a semi-circular central portion having one end integrally connect to said right wing, and a left wing integrally connect to said another end of said central portion, said right wing of said C-shaped top half mounting stand having a plurality of fastening holes, said central portion having a central limiting hole, said left wing having a bolt hole and a side limiting hole, said C-shaped bottom half mounting stand comprising a right wing, a semi-circular central indenting portion integrally connect to said right wing, and a left wing integrally connecting to said central indenting portion, said right wing of said C-shaped bottom half mounting stand having a plurality of fastening screw holes, and said left wing having a bolting hole, wherein said C-shaped top half mounting stand being connected to said C-shaped bottom half mounting stand by a plurality of screws passing through said plurality of fastening holes of said C-shaped top half mounting stand and screwing into said plurality of fastening screw holes of said C-shaped bottom half mounting stand, a bolt being screwed through said bolt hole of said left wing of said C-shaped top half mounting stand and said bolting hole of said left wing of said C-shaped bottom half mounting stand, so that said rotation displacement of said adjustable steamer arm is limited by said rotation displacement limiter, in which a vertical limiting screw is screwed through said central limiting hole and passed through said first elongated slot of said rotation displacement limiter, and that a horizontal limiting screw is screwed through said side limiting hole and passed through said second elongated slot of said rotation displacement limiter, therefore as said rotation displacement limiter is rotating, said adjustable steamer arm is rotated at a same distance.

18. A facial steamer, as recited in claim 11, wherein said mounting device comprises a main plate, a C-shape bottom half mounting stand integrally extended from an edge of said main plate, and a C-shape top half mounting stand, wherein by affixing said C-shaped top half mounting stand on said C-shaped bottom half mounting stand, a circular passage is formed therebetween for holding and mounting said rotation displacement limiter with said friction resistance ring therein, wherein said C-shaped top half mounting stand comprises a right wing, a semi-circular central portion having one end integrally connect to said right wing, and a left wing integrally connect to said another end of said central portion, said right wing of said C-shaped top half mounting stand having a plurality of fastening holes, said central portion having a central limiting hole, said left wing having a bolt hole and a side limiting hole, said C-shaped bottom half mounting stand comprising a right wing, a semi-circular central indenting portion integrally connect to said right wing, and a left wing integrally connecting to said central indenting portion, said right wing of said C-shaped bottom half mounting stand having a plurality of fastening screw holes, and said left wing having a bolting hole, wherein said C-shaped top half mounting stand being connected to said C-shaped bottom half mounting stand by a plurality of screws passing through said plurality of fastening holes of said C-shaped top half mounting stand and screwing into said plurality of fastening screw holes of said C-shaped bottom half mounting stand, a bolt being screwed through said bolt hole of said left wing of said C-shaped top half mounting stand and said bolting hole of said left wing of said C-shaped bottom half mounting stand, so that said rotation displacement of said adjustable steamer arm is limited by said rotation displacement limiter, in which a vertical limiting screw is screwed through said central limiting hole and passed through said first elongated slot of said rotation displacement limiter, and that a horizontal limiting screw is screwed through said side limiting hole and passed through said second elongated slot of said rotation displacement liniltor, therefore as said rotation displacement limiter is rotating, said adjustable steamer arm is rotated at a same distance.

\* \* \* \* \*